US005858366A

United States Patent [19]
Sodroski et al.

[11] Patent Number: 5,858,366
[45] Date of Patent: *Jan. 12, 1999

[54] IMMUNOGENIC PEPTIDES, ANTIBODIES AND USES THEREOF RELATING TO CD4 RECEPTOR BINDING

[75] Inventors: Joseph G. Sodroski, Medford; William A. Haseltine, Boston, both of Mass.; Udy Olshevsky, Remath-OAN, Israel; Eirik Helseth, Trondheim, Norway; Craig D. Furman, Nashua, N.H.

[73] Assignee: Dana-Farber Cancer Institute, Boston, Mass.

[ * ] Notice: The term of this patent shall not extend beyond the expiration date of Pat. No. 5,817,316.

[21] Appl. No.: 135,312

[22] Filed: Oct. 12, 1993

Related U.S. Application Data

[63] Continuation of Ser. No. 669,072, Mar. 14, 1991, abandoned, which is a continuation-in-part of Ser. No. 524,632, May 16, 1990, abandoned.

[51] Int. Cl.$^6$ ............... A61K 39/21; A61K 39/12; A61K 5/00; C07K 7/00
[52] U.S. Cl. ............... 424/188.1; 424/184.1; 424/204.1; 424/208.1; 530/324; 530/350; 530/331; 935/11
[58] Field of Search ............... 424/89; 530/324, 530/350, 331; 935/11

[56] References Cited

U.S. PATENT DOCUMENTS 5,109,123  4/1992  Reinherz et al. ............ 536/27

FOREIGN PATENT DOCUMENTS 0 279 688  2/1988  European Pat. Off. ....... A61K 37/02

OTHER PUBLICATIONS

Kim, Young–Woo, et al., J. of Immun. 144:1257–1262 (4) (1990).

Tschachler, E., et al., J. of Virol., 64(5):2250–2259 (1990).

Coffin, 1986, "Genehc Variation in AIDS Viruses" Cell 46:1–4.

Willey, et al, 1988, J. Virol. 62(1):139–147.

Willey, et al 1989 J. Virol. 63(9):3595–3600.

Ho, et al, 1988, Science 239:1021–1023.

Willey, et al, 1988, "In Vitro Mutagenesis Identifies a Region . . . " J. Virology 62(1):139–147.

Willey, et al, 1989, "Functional Interaction of Constant and Variable . . . " J. Virology 63(9);3595–3600.

Ho, et al, 1988, "Second Conserved Domain of gp120 . . . " Science, 239: 1021–1023.

Ho, et al., 1988, "Second Conserved Domain of gp120 is Important . . . " Science vol. 239: 1021–1023.

Ho, et al., 1987, "Human Immunodeficiency Virus Neutralizing . . . " J. Virology 61(6) : 2024–2028.

Mizukami, et al., 1988, "Binding Region for Human Immumodeficiency . . . " PNAS 85 : 9273–9277.

Cordonnier, et al., 1989, "Single Amino Acid Changes in HIV . . . " Nature 340: 571–574.

*Primary Examiner*—Lynette F. Smith
*Attorney, Agent, or Firm*—David G. Conlin; Ronald I. Eisenstein; Dike, Bronstein, Roberts & Cushman, LLP

[57] ABSTRACT

Immunogenic peptides containing amino acid residues which define a binding site to a CD4 receptor are disclosed. Antibodies to these peptides are also disclosed. Methods of reducing the ability of a gp12O env protein to bind to CD4 are also disclosed. Methods of treatment and prophylaxis using these antibodies and peptides are also described.

8 Claims, 8 Drawing Sheets

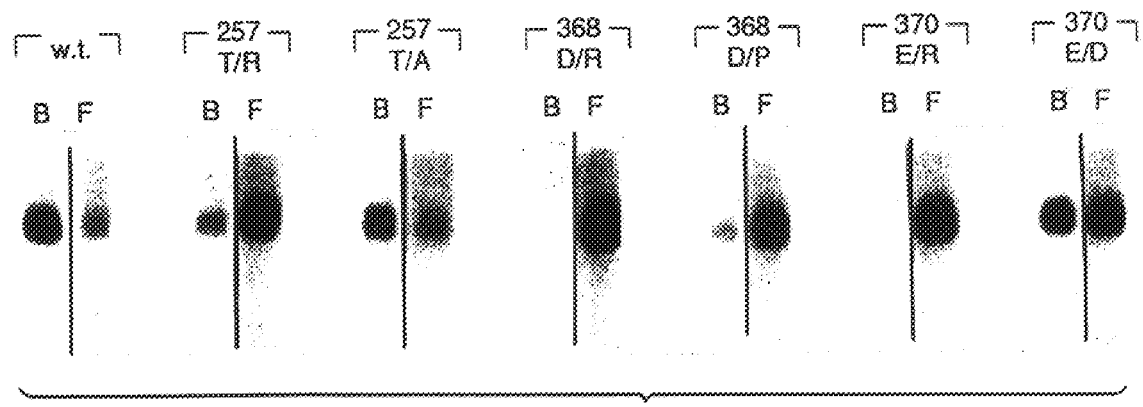
FIG. IA

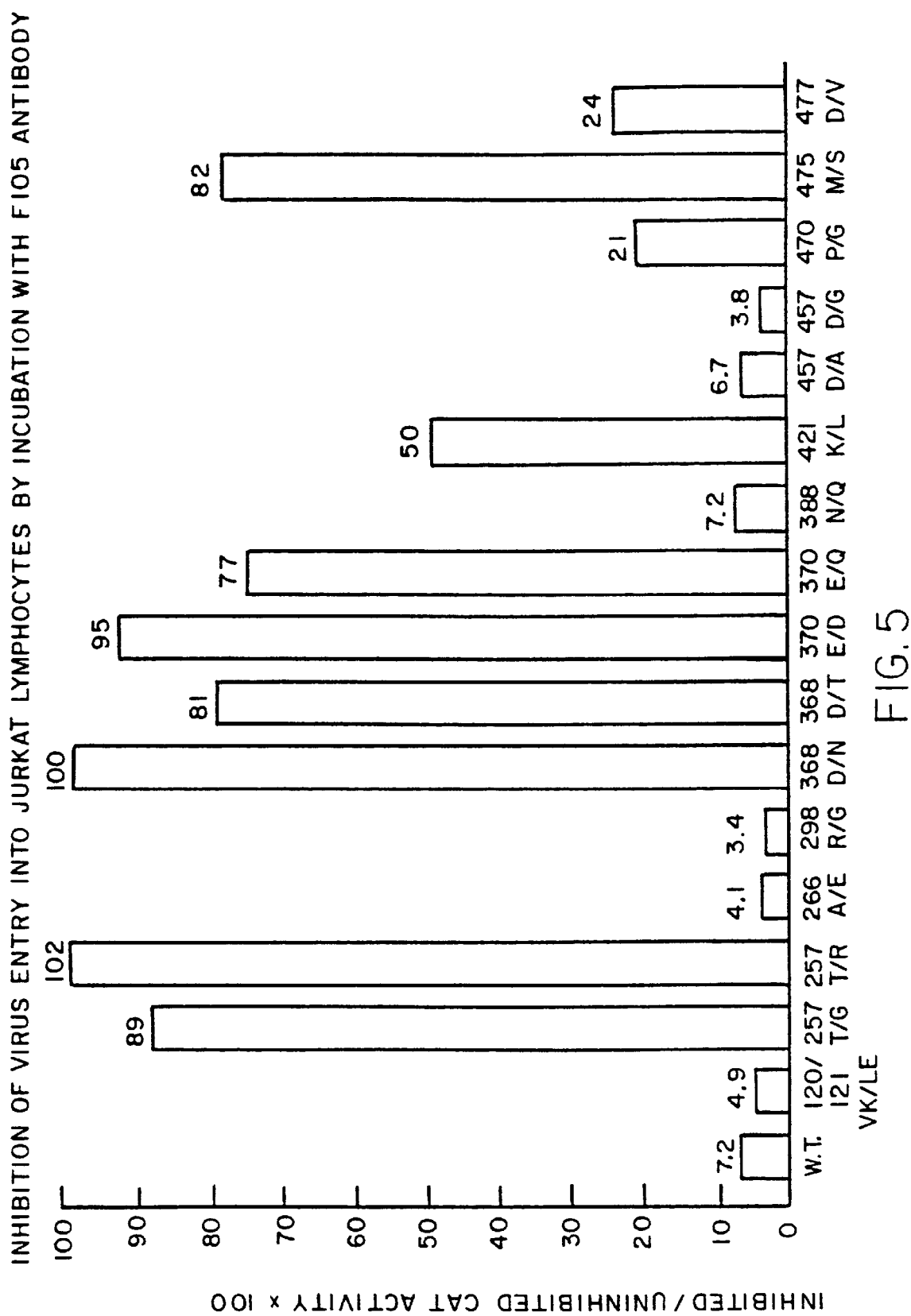

IMMUNOGENIC PEPTIDES, ANTIBODIES AND USES THEREOF RELATING TO CD4 RECEPTOR BINDING

This is a continuation of application Ser. No. 07/669,072 filed on Mar. 14, 1991 now abandoned, which is a "CIP" of Ser. No. 07/524,632, filed May 16, 1990 now abandoned.

The present invention is directed to immunogenic polypeptides, antibodies to such polypeptides, and uses thereof to prevent binding of gp120 protein with CD4 receptors.

The human immunodeficiency virus (HIV-I, also referred to as HTLV-III, LAV or HTLV-III/LAV) is the etiological agent of the acquired immune deficiency syndrome (AIDS) and related disorders. [Barre-Sinoussi, et al., Science 220:868–871 (1983); Gallo et al. Science 224:500–503 (1984); Levy et al., Science 225:840–842 (1984); Popovic et al., Science 224:497–500 (1984); Sarngadharan et al., Science 224:506–508 (1984); Siegal et al., N. Engl. J. Med. 305:1439–1444 (1981)]. This disease is characterized by a long asymptomatic period followed by the progressive degeneration of the immune system and the central nervous system. Studies of the virus indicate that replication is highly regulated, and both latent and lytic infection of the CD4 positive helper subset of T-lymphocytes occur in tissue culture, [Zagury et al., Science 231:850–853 (1986)]. The expression of the virus in infected patients also appears to be regulated as the titer of infectious virus remains low throughout the course of the disease. Molecular studies of the replication and genomic organization of HIV-I show that it encodes a number of genes [Ratner et al., Nature 313:277–284 (1985); Sanchez-Pescador et al., Science 227:484–492 (1985); Muesing et al., Nature 313:450–457 (1985); Wain-Hobson et al., Cell 40:9–17 (1985)]. Three of the genes, the gag, pol and env genes are common to all retroviruses. The genome also encodes additional genes that are not common to most retrovirus, the tat, rev (formerly referred to as art), nef, vif, vpr and vpu genes [Sodroski et al., Science 231:1549–1553 (1986); Arya et al., Science 229:69–73 (1985); Sodroski et al., Science 227:171–173 (1985); Sodroski et al., Nature 321:412–417 (1986); Feinberg et al., Cell 46:807–817 (1986); Haseltine, W. A., Journal of Acquired Immune Deficiency Syndrome 1:217–240 (1988); Cohen, E. et al., Nature 334:532–534 (1988); Wong-Staal, F., et al., AIDS Res. and Human Retro Viruses 3:33–39 (1987) which are all incorporated herein by reference.]

Nucleotide sequences from viral genomes of other retroviruses, particularly HIV-2 and simian immunodeficiency viruses, SIV (previously referred to as STLV-III), also contain the structural genes including env as well as regulatory sequences such as tat, rev and nef [Guyader et al., Nature 326:662–669 (1987); Chakrabarti et al., Nature 328:543–547 (1987), which is incorporated herein by reference].

The env genes of HIV-1, HIV-2 and SIV all produce an envelope glycoprotein, which is cleaved, with one portion being an exterior viral envelope protein subunit referred to as gp120. The binding and fusion of the HIV-1, HIV-2 and SIV viruses with cells is mediated by specific interaction between the external subunit of this gp120 viral envelope protein and the CD4 receptor on the target cell surface [Berger, E. A., et al., PNAS USA 85:2357–2361 (1988)].

One method that has been proposed to prevent or reduce HIV infection has been use of soluble CD4 molecules. However, this approach has not yet proven successfull clinically.

It would be useful if there was a means to specifically prevent the binding between the gp120 protein of HIV-1, HIV-2 or SIV in the CD4 region of the target cell.

Antibodies that can reduce the degree of binding of gp120 with the CD4 receptor would be useful.

Additionally, understanding of the specific interaction between the CD4 molecule and gp120 are important for treating immunodeficiency diseases.

SUMMARY OF THE INVENTION

We have now discovered immunogenic peptides having specified epitopes, which can be used to produce antibodies having specificity for binding sites on the env protein, gp120, of the HIV-1, HIV-2 or SIV viruses. These peptides can be used to produce antibodies which are characterized in that they bind specifically to certain designated epitopes of the gp120 protein. These epitopes are important for the binding of gp120 with CD4 receptors.

In accord with this invention, a method for treating or minimizing immunodeficiency diseases in mammals, particularly in humans, is disclosed. This method comprises eliciting the formation of an antibody to one of the HIV-1, HIV-2 or SIV epitopes by administering the immunogenic peptides disclosed or administering a therapeutic amount of an antibody to one of the HIV-1, HIV-2 or SIV epitopes disclosed herein.

BRIEF DESCRIPTION OF THE DRAWINGS

FIG. 1 shows the relative CD4 binding ability of gp120 mutants. FIG. 1A is a series of autoradiographs showing the amount of gp120 bound and unbound to the surface of SupT1 lymphocytes. FIG. 1B is a graph showing the $\log_{10}$ of the reduction in relative CD4 binding ability accompanying changes at specific amino acid sequences.

FIG. 2 is a sequence comparison of HIV-1, HIV-2, and SIV viruses near the 368/370 and 457 amino acid residues.

FIG. 5 shows the resistance to neutralization to a human monoclonal antibody to gp120 for some gp120 mutants.

DETAILED DESCRIPTION OF THE INVENTION

Figure 3:
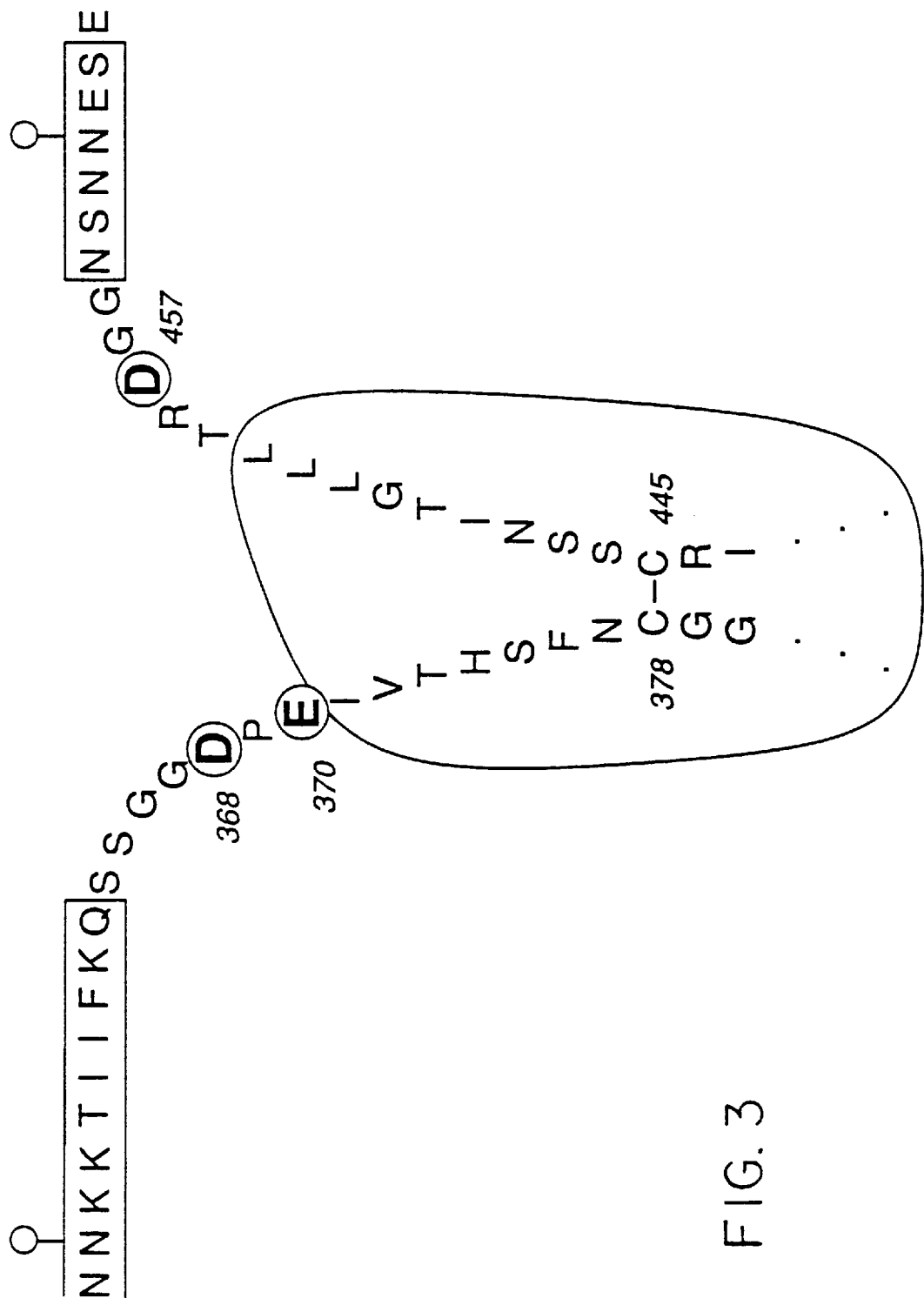
FIG. 3 is a schematic of the expected structure formed by the C3 and C4 regions of the gp120 envelope protein.

The binding of the CD4 receptor by the human immunodeficiency virus type 1 (HIV-1), type 2 (HIV-2) and simian immunodeficiency virus, (SIV), gp120 exterior envelope glycoproteins is important for virus entry and cytopathic effect [Dalgleish, A. G., et al., Nature 312:763–766 (1984); Klatzman, D., et al., Nature 312:767–769 (1984); McDougal, J., et al., Science 231:382–385 (1986); Lifson, J. D., et al., Nature 323:725–729 (1986); Sodroski, J. G., et al., Nature 321:412–417 (1986); Koga, Y., et al., J. Immunol. 144:94–102 (1990)]. Insertions or deletions in conserved gp120 regions C1, C3, C4 or C5 have been shown to affect CD4 binding [Lasky, L. A., et al., Cell 50:975–985 (1987); Kowalski, M., et al., Science 237:1351–1355 (1987); Cordonnier, A., et al., Nature 340:571–574 (1989); Cordonnier, A., et al., J. Virol. 63:4464–4468 (1989);

Linsley, P. S., et al., *J. Virol.* 62:3695–3672 (1988) which are incorporated herein by reference], although the effects of these changes on gp120 conformation was not examined. A proteolytic fragment composed of the 160 carboxy-terminal gp120 residues has been reported to bind CD4 [Nygren, A., et al., *Proc. Nat. Acad. Sci., U.S.A.* 85:6543–6546 (1988)], and antibodies directed against C4 or C5 were reported to be able to block CD4 binding in some circumstances [Lasky, P. S., et al., *Cell* 50, supra; Linsley, P. S., et al., *J. Virol.* 62, supra; Dowbenko, D., et al., *J. Virol.* 63:4703–4711 (1988); Sun, N. C., et al, *J. Virol.* 63:3579–3585 (1989); Ardman, B., et al., *J. AIDS* 3:206–214 (1990)]. However, the specific amino acids within these large regions that are critical for CD4 binding is not known.

Figure 1B:
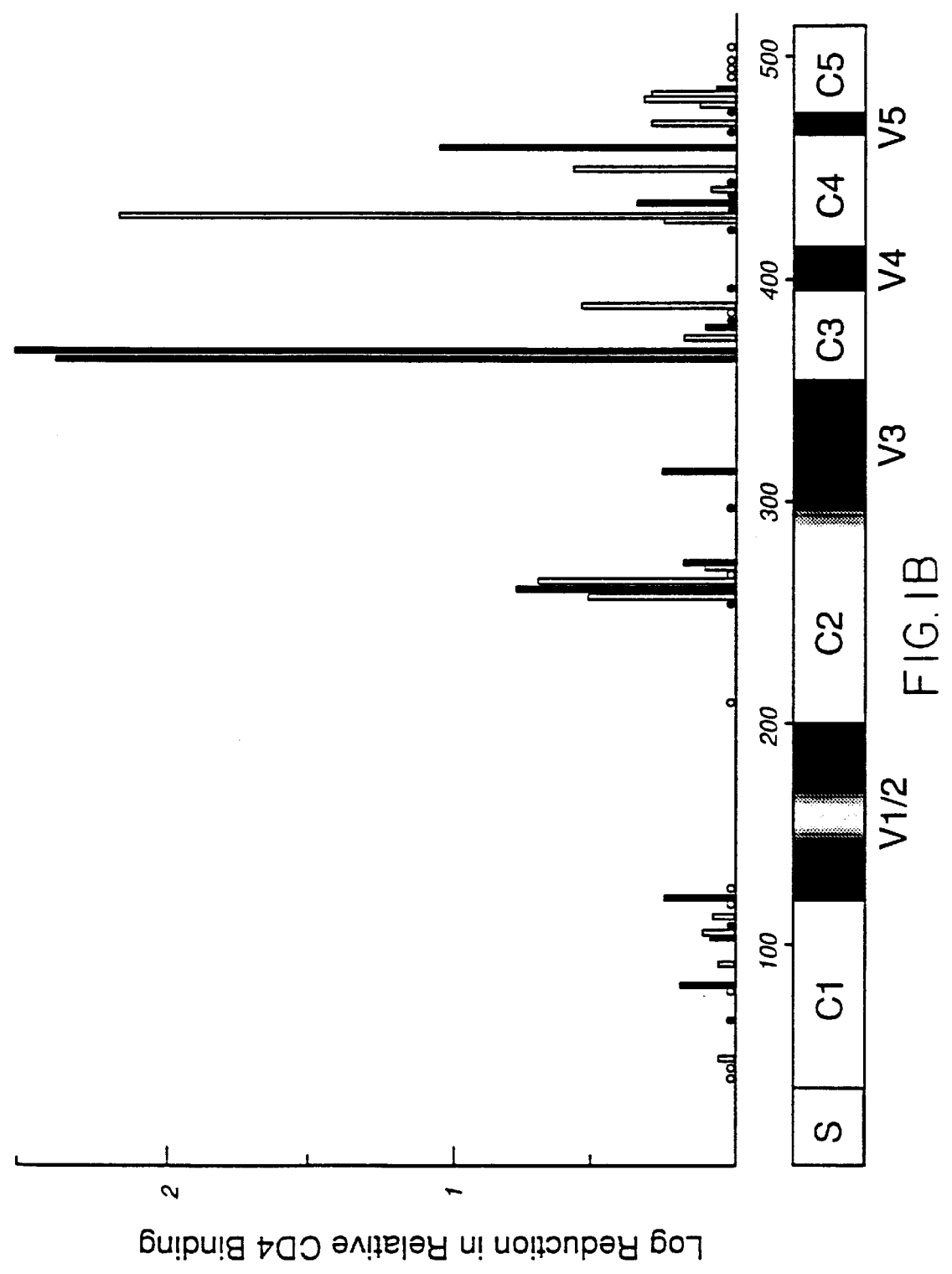

We have now discovered specific sites on the gp120 envelope protein that significantly affect its ability to bind CD4. These regions involve thr 257, asp 368, glu 370 and asp 457 (numbering is based upon HIV-1 gp120 sequences, with HIV-2 and SIV amino acid sequences matched to HIV-1, see, FIG. 2). Replacing these amino acids by site-directed mutagenesis resulted in certain cases in a greater than 90% reduction in the mutants' ability to bind with CD4 compared to that of the wild-type protein. (See FIG. 1). Accordingly, blocking any of these sites can drastically effect the ability of the gp120 protein to bind with CD4. Blocking the asp 368, the glu 370 or the asp 457 sites are preferred. Although not wishing to be bound by theory this is because they are predicted to be exposed to the aqueous environment on the native gp120 glycoprotein.

Blocking of these amino acids can be accomplished by any of a number of means well known to the skilled artisan such as antibodies specific to one of four epitopes, i.e. thr 257, asp 368, glu 370 or asp 457. For example, one obtains immunogenic polypeptides specific for any of these specified regions. Thereafter, the immunogenic polypeptide is used to generate antibodies specific to at least one of these binding sites (epitopes). In one preferred embodiment, the immunogenic polypeptide is used to generate antibodies, in vivo, in humans as discussed below. One can also use a peptide that contains more than one of these epitopes to create a large discontinuous epitope to raise an antibody to such a discontinuous epitope that will block more than one of these sites. Preferably, one would use a peptide, such as the gp120 mutant peptides described herein.

The presently described antibodies can be either monoclonal or polyclonal antibodies. Furthermore, as used herein, the term includes whole immunoglobulin as well as antigenic binding fragments thereof. In order to prepare such antibodies, one can use any of a number of well recognized techniques. For example, a peptide containing one of the four designated epitopes and a sufficient amount of flanking residues to define the characteristic epitope to which the antibody binds selectively can be used. As aforesaid, one can use a peptide containing more than one of these sites to create, in effect, a large discontinuous epitope. In one embodiment, it is preferred that the peptide used does not contain all the CD4 binding sites in the native protein (We refer herein to peptides which have amino acids that differ from native gp120 protein as gp120 mutants). The peptide can be chemically synthesized. Synthesis of peptides is well known in the art (See e.g., Merrifield, R. B., *Biochemistry* 3:1385–1390 (1960); U.S. Pat. No. 4,839,344 which are incorporated herein by reference). Commercial peptide synthesizers are available and can be used to generate the peptides.

The polypeptide must contain enough amino acid residues to define what is the epitope of the protein segment being detected but must not be so large as to have a definite conformation different from that of the protein being detected. However, if the peptide fragment is too short, the fragment will be found in irrelevant other proteins and might be physically buried in the immunizing carrier protein. Typically, a peptide to a single site or to closely spaced sites, such as for example, 368 and 370, will range from 5 to 18 amino acids. The exact size useful for a particular site can readily be determined by the skilled artisan from the present disclosure.

In order to increase its immunogenicity, the peptide may contain an amino acid such as cysteine near either end of the peptide, for example, at the first, second, last or penultimate position. The peptide may be conjugated to a carrier protein such as keyhole limpet hemocyanin or bovine serum albumin using glutaraldehyde [Walter, G., et al., *Proc. Natl. Acad. Sci. U.S.A.* 77:5197–5201 (1980) which is incorporated by reference] or through the cysteine residue [Carlson, J., et al., *Biochem. J.* 173:723 (1978) which is incorporated by reference]. The peptide:carrier protein conjugate is then injected into a host animal to generate the antibody. The preferred host animal is a human.

One preferred peptide will contain both the asp 368 and glu 370 residues as epitopes. Preferably, the antibodies generated are to the HIV-1 gp120. However, antibodies to the HIV-2 or SIV gp120 can readily be generated based on the present disclosure. See, for example, FIG. 2 which shows the strong degree of conservation at the 368 and 370 amino acid sequences in HIV-1, HIV-2 and SIV. In SIV strain MND, the glutamic acid is positioned 2 residues carboxy-terminal to the 370 position [Tsujimoto, H., et al., *Nature* 341:539–541 (1989) which is incorporated by reference]. There is also substantial sequence homology near the asp 457 position. Preferred immunogenic peptides according to this invention include as flanking amino acids the more conserved amino acids. For example, for the asp 368 or glu 370 from position 366–370, GGDPE. For asp 368 or glu 370 peptides that can be prepared include GGDPEITTH, GGDPEIVMH, SSGGDPEIVTH, SSGGDPEIVMH, SSGGDPEIVTHSFNC (all for HIV-1), or GKGSDPEVAYMWTNC (for HIV-2). For asp 457 peptides that can be prepared include CSSNITGLLLTRDGG, CSSNITGILLTRDGG, CSSNITGLLLTRDGGNSN (for HIV-1) or CNSTVTSIIANIDWQNN (for HIV-2). Other peptides that correspond in sequence to the amino acid sequences of other HIV-1, HIV-2 or SIV variants can also be used. Sequences that differ from these sequences as a result of conservative amino acid changes can also be used, as well as, peptides that differ by a few amino acids at either end from these examples.

Although the epitopes are near regions of high variability within the viruses, the immediately flanking amino acids are not as variable. The flanking amino acids used will depend upon the particular epitope or epitopes and gp120 that you wish to generate an antibody to, and can be determined readily by the person of ordinary skill in the art based upon this disclosure. Preferably, the peptide to one or two closely spaced sites is at least about 5 amino acids in length and no more than about 20 amino acids in length. Still more preferably, it is at least about 8 amino acids in length and no more than 18 amino acids in length. Even more preferably, the peptide is between 15 and 18 amino acids in length.

Figure 6:
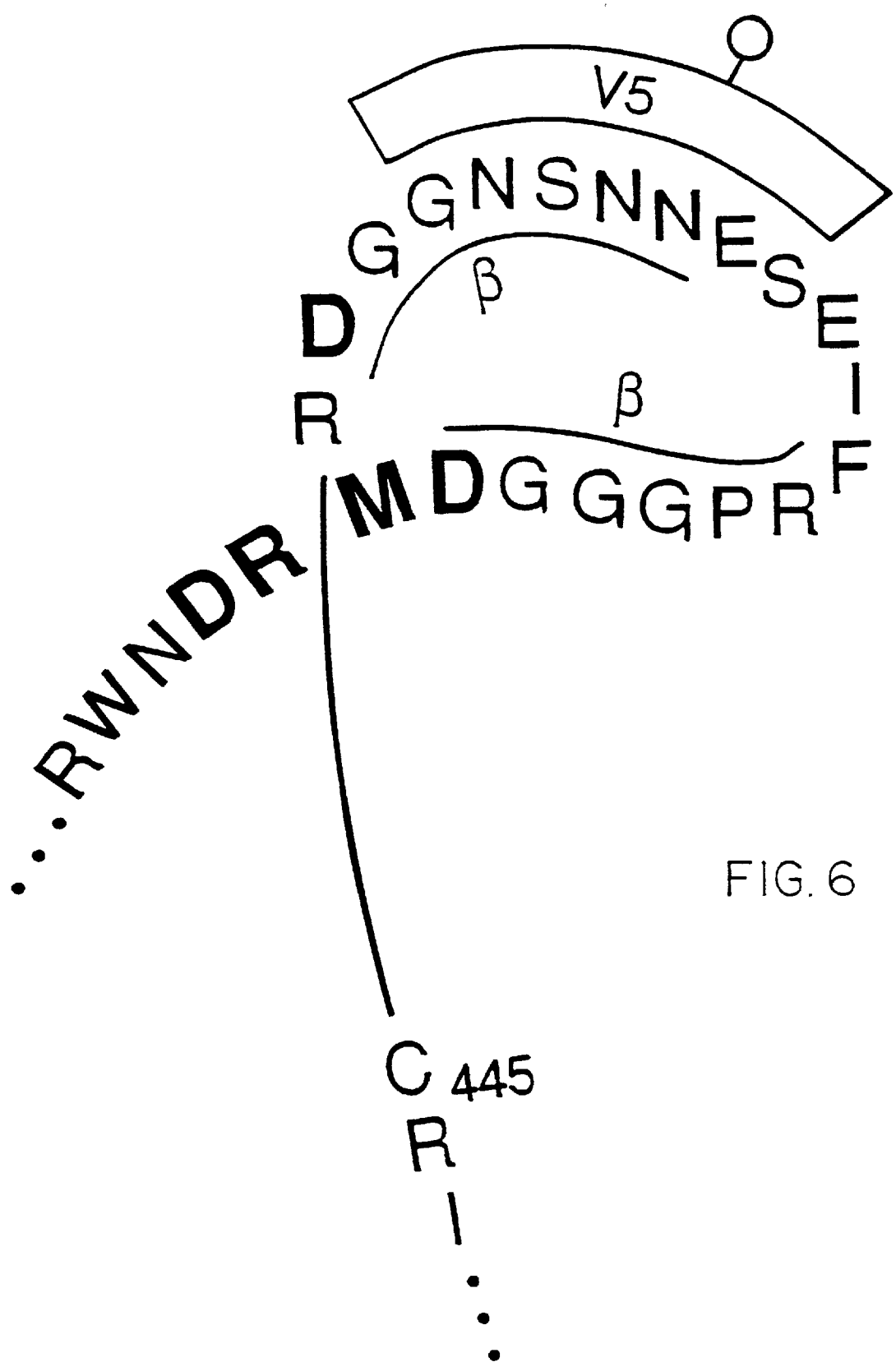
FIG. 6 is a schematic of the expected three-dimensional structure formed by β-loops near the V5 region of the gp120 envelope protein.

It is also preferable to generate an antibody to a discontinuous epitope that arises from a number of individual epitopic elements. We have found that some antibodies seem to react strongly to sites adjacent to CD4-binding sites. For example, F105, a human monoclonal antibody derived from HIV-1 infected individuals that recognizes the gp120 glycoprotein from a diverse range of HIV-1 isolates (from Marshall Posner), seems to recognize changes at amino acids 256–257, 368–370, 421 or 470–484. Thus, amino acid changes in HIV-1 gp120 residues located in four discontinuous regions can result in dramatic reductions in recognition by this broadly neutralizing antibody. Using gp120 mutants containing multiple substitutions in the above residues reduced F105 recognition with an apparent absence of global confirmational changes of the gp120 mutants, certain of the mutants escaped functional neutralization by the antibody. Two of the elements that form the discontinuous epitope are 256–257 and 368–370 which contain three of the above-described CD4 epitopic binding sites. Recognition by the F105 antibody was more sensitive to different substitutions at these residues, than was CD4 binding. A third element of the discontinuous epitope is lysine 421, which is adjacent to tryptophan 427. Changes in tryptophan 427 result in dramatic reductions in CD4 binding ability, but not F105 recognition. Thus, the antibody apparently recognizes a more hydrophilic segment in the fourth conserved gp120 region than does CD4. A fourth CD4 epitopic region effecting CD4 binding, aspartic acid 457, does not appear to affect the antibody's recognition, but there are reasons to believe that this site is proximal on the native gp120 glycoprotein with another element which forms part of the discontinous epitope, which is at gp120 residues 470–484. Both hydrophilic regions, which symmetrically flank the short fifth variable region of gp120, exhibit strong β-turn potential, which we believe can result in the apposition of these regions in the native glycoprotein so that residues 470–484 are proximal to the region near aspartic acid 457 (See FIG. 6). In this figure, it is shown how the first turn at 457 (DGGNSNN . . . ) is near this second turn at 474–478 (DMRD), when one looks at the predicted three-dimensionional structure of gp120. Indeed, some of the more conformationally disruptive changes in aspartic acid 457 (e.g., 457 D/R) affects antibody recognition, whereas some of the more conformationally disruptive changes in the 470–484 regions (e.g., 477 D/V or 482/483/484 ELY/GRA) exhibit small effects on CD4 binding.

Thus, it can be useful to use gp120 proteins that contain most of this discontinuous epitope in generating antibodies. Preferably, one uses a mutant gp120 protein, wherein there is a change in the amino acid residues to create increased exposure of the desired epitope to generate such an antibody. Examples of how to increase the exposure of the discontinuous epitope are: (1) to remove variable regions from the gp120 molecule, yet retain an overall conformation approximating that of the wild-type protein; (2) to remove particular sugar addition sites; and, (3) to make single amino acid changes in gp120 residues that are near the linear components of the epitope. As used herein, "near" refers to proximal on the three-dimensional structure of gp120.

The variable regions of the gp120 protein are known. One would preferably remove portions of one or more variable regions. For example, the mutant gp120 protein (or peptide) Δ119–205 has the V1 and V2 regions removed, thereby increasing exposure to, for example, the discontinuous epitopic region recognized by the F105 antibody. One can remove other variable regions. Once can readily determine empirically by known methods such as immunoprecipitation based upon the present disclosure, whether a particular deletion increases exposure of the desired epitope.

With respect to sugar addition sites, the sugar addition sites "near" a desired epitope or epitopic element of a desired discontinuous epitope are preferably removed. For example, the sites at 356 or 262. These sites can be removed by methods well known in the art. For example, a sugar addition site has the sequence NX(T or S), where X is any amino acid. Site directed mutagenesis of N or (T or S) to a different amino acid will remove the sugar addition site. For example, the mutant gp120 protein 356 N/I.

Preferably, one would combine more than one of these different amino acid changes or deletions. In addition, it is possible to delete and/or change other portions of the protein that do not adversely affect the conformational structure of the epitope (e.g. changes at the N-terminus).

Mutants that result from changes in at least one of the following sites are one preferred grouping:

266, 356, 381, 427, 432, 435, 438, 493 and 495.

Preferably, one would use the following mutants: 119–205, 266 A/E, 356 N/I, 381 E/P, 427 W/S, 427 W/V, 432 K/A, 435 Y/H, 438 P/R, 493 P/K, and 495 G/K.

In generating the above peptides, one can use a variety of methods well known in the art. For example, one could take native gp120 proteins and by site-directed mutagenesis create gp120 mutants. Alternatively, or in combination with the above, one could use a protein which corresponds to an HIV gp120 protein and cleave non-essential regions. Alternatively, one could use standard protein synthesis to synthesize a peptide that contains the discontinuous epitopic region.

In a preferred embodiment the immunogenic peptides can be used to elicit antibodies which are specific to at least one of the CD4 binding sites on gp120. These peptides can be used for immunoprophylaxis or immunotherapy. For example, administration of these peptides containing binding sites corresponding to HIV-1 or HIV-2 gp120 to an HIV naive individual will result in antibodies to the described binding sites of gp120 env protein being produced that will hinder or prevent HIV infection of that individual. In an infected individual, the in vivo production of these antibodies, which differ from antibodies to the complete gp120 env protein, can help prevent or delay further infection of other cells. Preferably, one would use combinations of peptides to the different epitopes in order to elicit a series of antibodies. As aforesaid, the peptides can be conjugated to another moiety, e.g. a carier protein, which will increase the immunogenicity of the peptide.

In an alternative embodiment one can prepare the antibody in a host animal other than the individual to be treated. The antibody generated from these peptides can be polyclonal or monoclonal depending upon the particular application for which it is designed and/or the variability of the protein near the epitope. As aforesaid, these antibodies can be prepared by techniques well know to the skilled artisan. For example, the desired fragment of the protein or chemically synthesized peptide can be conjugated to keyhole limpet hemocyanin (KLH) and used to raise an antibody in an animal such as a rabbit. Typically, the peptide-KLH conjugate is injected several times over a period of about two months to generate antibodies. Mutant gp120 glycoproteins as described above, which exhibit increased exposure of the defined gp120 regions to antibodies, can be synthesized and inoculated into animals or humans. Antibodies are then collected from serum by standard techniques. Alternatively, monoclonal antibodies can be produced in cells which produce antibodies to the peptide by using standard fusion techniques for forming hybridoma cells. [Kohler, G., et al., *Nature* 256:495 (1975) which is incorporated by reference]. Typically, this involves fusing an antibody producing cell with an immortal cell line such as a myeloma cell to produce the hybrid cell. In another method, monoclonal antibodies can be produced from cells by the method of Huse, et al, *Science* 246:1275 (1989) which is incorporated herein by reference.

In one example, hybridomas can be generated by immunization of mice with one of the immunogenic peptides. The mice can be immunized intraperitoneally (i.p.) with a sufficient amount of peptide. This can then be followed immediately by an i.p. injection of, for example, cyclophosphamide in $H_2O$. The cyclophosphamide treatment is repeated one and two days following the primary injection. About two weeks following immunization, mice are again injected with a sufficient amount of the peptide and then allowed to rest for another two weeks. Four days following the second injection, the animals are sacrificed and their spleens obtained for the first fusion.

Hybridomas are produced by fusing cells by typical techniques, such as from immunized mice with SP2/O myeloma cells by a polyethylene glycol (PEG) method. Cells are aseptically removed from immunized mice and a single cell suspension of the spleen cells obtained by perfusing the spleen with serum-free media (e.g. DME). Spleen cells and myeloma cells are mixed together at a ratio, for example, 5 to 1, spleen cells to myeloma cells. The cells are then centrifuged and the supernatant removed by aspiration. The cells are then grown in medium by standard techniques. Hybridomas, which grow after the fusion procedure, are then screened for secretion of antibodies specific to the gp120 epitopes by an ELISA assay on a cell lysate. Hybridomas, that produce positive results, are expanded and cloned by limiting dilution to assure that the cells and resulting antibodies are indeed, monoclonal. Hybridoma colonies that test positive for the presence of antibody to one of the desired gp120 epitopes are diluted in media to a concentration of, for example, 5 hybridoma cells per mililiter. Once colonies grow, the supernatants are again tested for the presence of antibody to the gp120 epitope. If the results are positive when tested by an ELISA assay, the colonies are cloned again by limiting dilution.

Both the peptides and the antibodies raised by such peptides against the gp120 epitopes of the HIV-1, HIV-2 or SIV virus can be used to prevent or minimize infection of cells by the virus. Preferably, the cells are human cells. This method comprises administering a therapeutically effective amount of either the peptide or the antibody to a fluid or cell sample from a mammal suspected of having the virus. Preferably, one uses a body fluid sample. Preferably, the mammal is a primate, more preferably, it is a human. When used in vivo for therapy, the antibodies of the present invention are administered to the patient in an amount that eliminates or reduces the ability of the virus to enter other cells. The antibody acts to block binding site of the gp120 protein and thereby reduce the viruses ability to enter a cell and reproduce. The peptide or mutant protein is administered in a sufficient amount to raise enough antibodies to reduce or eliminate the ability of the virus to enter the cell. Cocktails of combinations of both peptides and/or antibodies according to this invention can also be used.

The antibody or peptide can be delivered by any of a number of means. For example, either can be administered by parenteral injection (intramuscular (i.m.), intraperitoneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The antibodies and peptides will preferably be formulated in a unit dosage form.

For example, solid dose forms that can be used for oral administration include capsules, tablets, pills, powders and granules. In such solid dose forms, the active ingredient, i.e., antibody or peptide, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

These antibodies may also be used as carriers. As such, they may be used to deliver a desired chemical moiety to the epitope on gp120. For example, they may be used to deliver a cytotoxic drug or an enzymatically active material of, for example, bacterial or plant origin. For example, delivering an enzyme that will cleave the gp120 at one of these sites, and thus, delete the binding site, would be particularly advantageous. In another embodiment, these antibodies can be used to deliver another molecule which will cap the site or an adjacent site. This would be particularly useful with antibodies to either the 368 or 370 site of the viral gp120 virus. Any molecule that will hinder the binding of gp120 to CD4 receptors can be used. Indeed, the use of labels, such as discussed below, can enhance the antibody's ability to prevent or hinder binding with the CD4 receptor.

In addition to using antibodies to block these binding epitope sites, other means of blocking these sites can be used. For example, although the 368–370 and 457 residues appear to be a large distance apart based upon a linear 120 amino acid sequence, we expect they are proximal on the native molecule. See, FIG. 3. This model is based on the observation that the gp120 cysteine residues at 378 and 445 are disulfide-linked, and accordingly, the two regions can form the structure shown. Furthermore, all three residues, namely the 368, 370 and 457 residue are located within hydrophilic regions exhibiting a strong potential to form β-turns. This property and the relative placement show that chemical means of blocking these sites in addition to the antibodies can be used. Thus, a method of administering an effective amount of a material, e.g., a chemical moiety, to block the three sites can also be used. As aforesaid, there are other regions that are also proximal to these sites and which are similarly affected.

These antibodies can also be labelled to be used in immunoassay procedures to detect the presence of the gp120 protein and thus the virus in a patient or to monitor the status of the virus in a patient diagnosed as having the virus. Further, as mentioned above the label can also provide some more steric hinderances to the antibody to enhance its ability to prevent binding of the gp120 to the CD4 receptor. When used to monitor the status of the disease, a quantitative immunoassay procedure should be used. For example, it can be used to track the treatment of the disease by these antibodies. The immunoassays can readily be determined by the person of ordinary skill in the art.

It is possible to determine both the level of gp120 and whether there has been a change in that level. One can compare results against base line levels obtained for the material being sampled. Further, one can take samples from the same individual at various times to provide continuing levels of comparison.

In accordance with this invention, an antibody or cocktail of probes, e.g. antibody probes, can be used for detection. The probes, e.g. antibodies, can be labelled directly with a reporter or indirectly with a member of a specific binding pair using conventional techniques.

Specific binding pairs can be of the immune or non-immune type. Immune specific binding pairs are exemplified by antigen-antibody systems of hapten/anti-hapten systems. These include fluorescein/anti-fluorescein, dinitrophenyl/anti-dinitrophenyl, biotin/anti-biotin, peptide/anti-peptide and the like.

Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; bitoin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxy-succinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfdhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labelled probe, e.g., antibody, detectably-labelled antibodies, or detectably-labelled member of the specific binding pair is coupled to a reporter which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reduction methylation for $^{3}H$.

Enzymes suitable for use in this invention include, but are not limited to, horseradish peroxidase, alkaline phosphatase, β-galactosidase, glucose oxidase, luciferase, β-lactamase, urease and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, *Immunochemistry* 8:871 (1971), Avrameas and Ternynck, *Immunochemistry* 8:1175 (1975), Ishikawa et al., *J. Immunoassay* 4 (3):209–327 (1983) and Jablonski, *Anal. Biochem.* 148:199 (1985), which are incorporated by reference.

Labeling can be accomplished by indirect methods such as using spacers or other members of specific binding pairs. An example of this is the detection of a biotinylated antibody with unlabelled streptavidin and biotinylated enzyme, with streptavidin and biotinylated enzyme being added either sequentially or simultaneously. Thus, according to the present invention, the antibody used to detect can be detectably-labelled directly with a reporter or indirectly with a first member of a specific binding pair. When the antibody is coupled to a first member of a specific binding pair, then detection is effected by reacting the antibody-first member of a specific binding complex with the second member of the binding pair which is labelled or unlabelled as mentioned above.

Moreover, the unlabelled detector antibody can be detected by reacting the unlabelled antibody with a labelled antibody specific for the unlabelled antibody. Such an anti-antibody can be labelled directly or indirectly using any of the approaches discussed above. For example, the anti-antibody can be coupled to biotin which is detected by reacting with the streptavidin-horseradish peroxidase system discussed above.

One preferred embodiment utilizes biotin. The biotinylated antibody is in turn reacted with streptavidin-horseradish peroxidase complex. Orthophenylenediamine, 4-chloro-naphthol, or tetramethylbenzidine (TMB) can be used to effect chromogenic detection.

The preferred immunoassay format for practicing this invention is a forward sandwich assay in which the capture reagent has been immobilized, using conventional techniques, on the surface of the support. Suitable supports used in assays include synthetic polymer supports, such as polypropylene, polystyrene, substituted polystyrene, e.g., aminated or carboxylated polystyrene; polyacrylamides; polyamides; polyvinylchloride, etc.; glass beads; agarose; nitrocellulose, etc.

The present invention is further illustrated by the following examples. These examples are provided to aid in the understanding of the invention and are not to be construed as a limitation thereof.

EXAMPLES

COS-1 cells were transfected by the DEAE-dextran procedure of Cullen, B. R., *Meth. Enzymol.* 152:684–703 (1987) with ten micrograms of pSVIIIenv plasmid containing either the wild-type or mutated HXB2 env gene. The pSVIII env plasmid allows a high level of transient expression of gp160 envelope precursor [Helseth E., et al., *J. Virol.* 64:2416–2420 (1990) which is incorporated herein by reference]. Forty-eight hours after transfection, cells were labelled with $^{35}$S-cysteine. For gp160 mutants that undergo proteolytic cleavage, the mature gp120 exterior envelope glycoprotein can be detected in supernatants of transfected COS-1 cells, due to the lability of gp120 association with the gp41 transmembrane glycoprotein. Radiolabelled gp120 present in transfected COS-1 cell supernatants was used to assess the ability to bind to the CD4 molecule on the surface of SupT1 lymphocytes. Labelled supernatants were incubated with $5 \times 10^7$ SupT1 lymphocytes at 37° C. for one hour. The SupT1 cells were washed once with phosphate-buffered saline, lysed in 1.0 ml RIPA lysis buffer, and used for immunoprecipitation with excess 19501 AIDS patient serum as described in Helseth, E., et al., *J. Virol.* 64, supra.

Precipitates were analyzed on SDS-polyacrylamide gels and the autoradiograms quantitated by densitometry as described below. Pilot studies using these procedures except pre-incubating the cells with OKT4a (Ortho Diagnostics) prior to gp120 or the mutant gp120 binding demonstrated that gp120 binding to SupT1 lymphocytes was completely blocked by OKT4a monoclonal antibody, indicating dependence on the CD4 molecule.

The KpnI-BamH1 fragment of the pSVIIIenv plasmid was used for site-directed mutagenesis according to the procedure of Kunkel, T. A., et al., *Meth. Enzymol.* 154:367–382 (1987). The presence of the mutation was confirmed by the generation of a novel restriction endonuclease site in some cases and by DNA sequencing as in Sanger, F., et al., *Proc. Natl. Acad. Sci., U.S.A.* 12:5463–5467 (1977). Two independent clones of each mutated env fragment were prepared and used for the CD4 binding assay to ensure that spontaneous mutations distant from the desired mutation were not responsible for the observed phenotypes. The number of the mutant in Table 1 refers to the envelope glycoprotein amino acid residue of the HXBc2 strain of HIV-1, where 1 is the initial methionine [Myers, G., et al. (eds), *Human Retroviruses and AIDS* (Los Alamos National Laboratory, N.M.) (1988) which is incorporated herein by reference].

Bound and free forms of wild-type and mutant gp120 were measured by immunoprecipitation of radiolabelled proteins using excess 19501 AIDS patient antiserum, analyzing the proteins on SDS-polyacrylamide gels and densitometrically scanning the gp120 bands. All of the CD4 binding experiments were performed under conditions where the CD4 concentration was not limiting for gp120 binding (data not shown) so that the calculated relative binding ability approximates the true ratio of mutant:wild-type binding constants. The ratio of bound:free gp120 was measured over a greater than twenty-fold range of gp120 concentrations and did not vary. In separate experiments, the relative CD4 binding ability did not vary more than 10 per cent of the value reported. Relative binding ability for these results was calculated from the following formula.

$$\text{Relative binding ability} = \frac{[gp120 \text{ bound}]_{mutant} \times [gp120 \text{ free}]_{wild-type}}{[gp120 \text{ free}]_{mutant} \times [gp120 \text{ bound}]_{wild-type}}$$

Amino acids conserved among HIV-1, HIV-2, SIVmac, and SIVagm gp120 exterior envelope glycoproteins that were altered in this study are shown in Table 1.

Table 1

| CD4-Binding ability of HIV-1 gp120 Mutants | |
|---|---|
| Amino Acid change[a] | Relative CD4 binding ability[b] |
| Wild type | 1.00 |
| 36 V/L | 1.44 |
| 40 Y/D | 1.23 |
| 45 W/S | 0.84 |
| 69 W/L | 1.36 |
| 76 P/Y | 1.36 |
| 76 P/N | 1.16 |
| 80 N/R | 0.62 |
| 83 E/R | NP[c] |
| 83 E/Y | NP[c] |
| 88 N/P | 0.89 |
| 91 E/R | 1.21 |
| 93/94 FD/TR | NP[c] |
| 102 E/L | 0.82 |
| 103 Q/F | 0.62 |
| 106 E/A | 1.53 |
| 113 D/A | 1.16 |
| 113 D/R | 0.85 |
| 117 K/W | 1.06 |
| 120/121 VK/LE | 0.51 |
| 125 L/G | 1.31 |
| 207 K/W | 1.02 |
| 227 K/E | NP[c] |
| 252 R/W | 2.5 |
| 256 S/Y | 0.30 |
| 256 S/R | NP[c] |
| 257 T/R | 0.16 |
| 257 T/A | 1.12 |
| 257 T/G | 1.04 |
| 259 L/K | NP[c] |
| 262 N/T | 0.21 |
| 266 A/E | 0.97 |
| 267 E/L | 0.76 |
| 269 E/L | 0.61 |
| 298 R/G | 1.00 |
| 314 G/W | 0.54 |
| 368 D/R | <0.004 |
| 368 D/P | 0.09 |
| 368 D/T | 0.33 |
| 370 E/R | <0.003 |
| 370 E/D | 0.45 |
| 377 N/K | 0.69 |
| 380 G/F | 0.78 |
| 381 E/P | 1.09 |
| 382 F/L | 2.7 |
| 384 Y/E | 0.29 |
| 391 F/Q | NP[c] |
| 395 W/S | 1.11 |
| 420 I/R | 1.24 |
| 421 K/L | 0.55 |
| 435 Y/H | 1.43 |
| 435 Y/S | 0.77 |
| 438 P/R | 2.3 |
| 447 S/I | 0.27 |
| 457 D/A | 0.09 |
| 470 P/L | 0.54 |
| 474 D/A | 1.01 |
| 475 M/S | 1.03 |
| 476 R/D | 0.71 |
| 477 D/R | NP[c] |

Table 1-continued

CD4-Binding ability of HIV-1 gp120 Mutants

| Amino Acid change[a] | Relative CD4 binding ability[b] |
|---|---|
| 477 D/V | 0.39 |
| 477 D/S | 0.53 |
| 482/483/484 ELY/GRA | 0.44 |
| 485 K/V | 0.79 |
| 486/487 YK/WP | NP[c] |
| 491 I/F | 1.28 |
| 493 P/K | 1.78 |
| 495 G/K | 1.71 |
| 497/498/499 APT/VLL | 0.98 |
| 500/501 KA/KGIPKA | 0.91 |

[a]The mutations result in substitution of the amino acid(s) on the right for the amino acid(s) on the left; for example, 273 R/I indicates a substitution of isoleucine for the arginine residue at position 273. Single letter amino acid abbreviations used are as follows: A, Ala; C, Cys; D, Asp; E, Glu; F, Phe; G, Gly; M, Mis; I, Ile; K, Lys; L, Leu; M, Met; N, Ash; P, Pro; Q, Gln, R, Arg; S, Ser; T, Thr; V, Val; W, Trp; and Y, Tyr.
[b]The relative CD4 binding ability was calculated using the following formula:

$$\text{Relative binding ability} = \frac{[\text{gp120 bound}]_{mutant} \times [\text{gp120 free}]_{wild\text{-}type}}{[\text{gp120 free}]_{mutant} \times [\text{gp120 bound}]_{wild\text{-}type}}$$

[c]Inefficient processing of the gp120 precursor to gp120 and gp41 glycoproteins was observed for these mutants. CD4 binding ability was not determined.

The processing index is a measure of the conversion of mutant gp160 envelope glycoprotein precursor to mature gp120, relative to that of the wild-type glycoprotein.

Transfected COS-1 cells were continuously labelled with $^{35}$S-cysteine for twelve hours as described above, and cell lysates and supernatants were immunoprecipitated with AIDS patient serum as described above. The amounts of gp160 and gp120 glycoproteins were determined by densitometric scaning of autoradiograms of SDS-polyacrylamide gels with the processing index calculated according to the formula:

$$\text{Processing index} = \frac{[\text{Total } gp120]_{mutant} \times [gp160]_{wild\text{-}type}}{[gp160]_{mutant} \times [\text{Total } gp120]_{wild\text{-}type}}$$

The association index, which is a measure of the association between the mutant gp120 molecule and the gp41 molecule on the envelope-expressing COS-1 cells, relative to that of the wild-type glycoproteins, was then calculated. Cell lysates and supernatants were treated as described above and the index calculated according to the formula:

$$\text{Association Index} = \frac{[\text{Cell } gp120]_{mutant} \times [\text{Supernatant } gp120]_{wild\text{-}type}}{[\text{Supernatant } gp120]_{mutant} \times [\text{Cell } gp120]_{wild\text{-}type}}$$

The results are shown in Table 2 below.

TABLE 2

Characterization of Selected gp120 Mutants

| Mutant | Relative CD4 Binding[a] | Processing Index[b] | Association Index[c] |
|---|---|---|---|
| Wild-type | 1.00 | 1.00 | 1.00 |
| 256 S/Y | 0.30 | 0.17 | 0.17 |
| 257 T/R | 0.16 | 0.43 | 1.00 |
| 262 N/T | 0.21 | 0.07 | 0.14 |
| 368 D/P | 0.09 | 0.94 | 0.91 |
| 368 D/T | 0.33 | 0.86 | 0.93 |
| 368 D/R | <0.004 | 0.79 | 0.97 |
| 370 E/R | <0.003 | 0.67 | 9.85 |
| 370 E/D | 0.45 | 0.93 | 0.99 |
| 384 Y/E | 0.29 | 1.00 | 0.35 |
| 447 S/I | 0.27 | 0.07 | 0.29 |
| 457 D/A | 0.09 | 0.88 | 0.76 |
| 477 D/V | 0.39 | 0.20 | 1.00 |
| 482,3,4 ELY/GRA | 0.44 | 0.23 | 0 |

[a]Values for relative CD4-binding ability were obtained from Table 1.
[b]$\text{Processing index} = \frac{[\text{Total gp120}]_{mutant} \times [\text{gp160}]_{wild\text{-}type}}{[\text{gp160}]_{mutant} \times [\text{Total gp120}]_{wild\text{-}type}}$
[c]$\text{Association Index} = \frac{[\text{Cell gp120}]_{mutant} \times [\text{Supernatant gp120}]_{wild\text{-}type}}{[\text{Supernatant gp120}]_{mutant} \times [\text{Cell gp120}]_{wild\text{-}type}}$ Using these methods, we changed every gp120 amino acid that is conserved among primate immunodeficiency viruses that bind CD4 and were able to define gp120 binding sites. Changes in three gp120 residues (asp 368 and glu 370 in the C3 region and asp 457 in the C4 region) resulted in glycoproteins that exhibited greater than 90 per cent reduction in CD4 binding, even though precursor processing, subunit association and monoclonal antibody recognition were similar to those of the wild-type glycoprotein. These three acidic residues are located in gp120 regions that share the features of hydrophilic character, strong propensity for β-turn formation, predicted potential to act as a B cell epitope, and proximity to a glycosylated hypervariable region [Myers, G., et al., *Human Retroviruses and AIDS*, supra; Modrow, S., et al., *J. Virol* 61:570–578 (1987)].

FIG. 1A shows several examples of the results, which were used to calculate the CD4-binding abilities of the mutant gp120 glycoproteins, see Table 1 and FIG. 1B. FIG. 1A shows the amount of gp120 bound (B) to the surface of SupT1 lymphocytes, as well as the unbound (F) gp120, for both wild-type and mutant glycoproteins.

In FIG. 1B the $\log_{10}$ of the reduction in relative CD4 binding ability observed for the most disruptive change at a given amino acid residue is shown. The open bars indicate mutant glycoproteins that exhibited processing or association indices less than 40 per cent of those of the wild-type glycoproteins. The dark bars represent mutant glycoproteins for which both processing and association indices were at least 40 per cent of the wild-type values. The linear sequence of the HIV-1 gp120 molecule is shown, with the conserved regions in light and the variable regions shaded dark. Numbers indicate amino acid residues. S=signal sequence.

With nine exceptions, all of the mutant envelope glycoproteins were processed to gp120 molecules detected in the COS-1 cell supernatants. Even though most of the introduced amino acid changes were not conservative, the majority of gp120 mutants exhibited CD4 binding ability that did not differ more than two-fold from that of the wild-type glycoprotein. These results indicate that the majority of well-conserved gp120 residues are not per se essential for high-affinity CD4 binding.

Figure 4A:
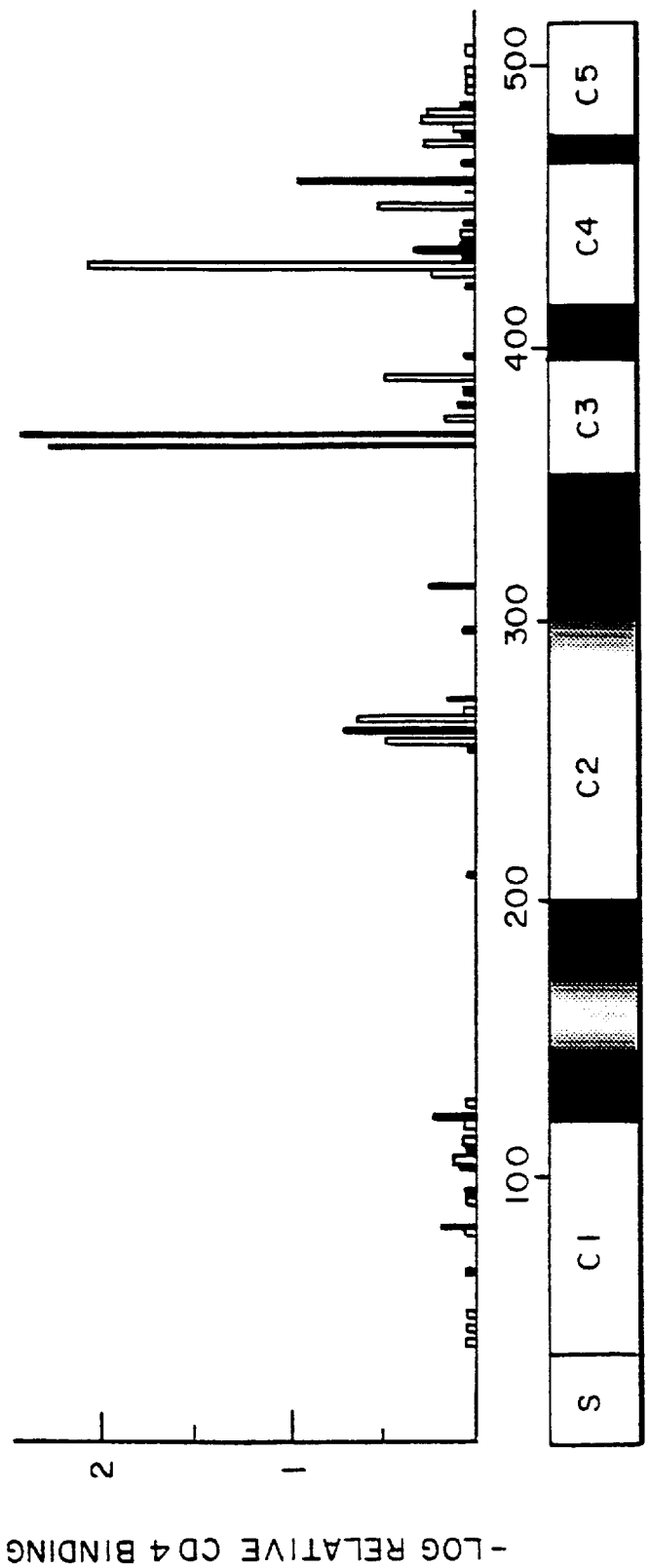
FIGS. 4A and 4B show the effect of amino acid changes in HIV-1 gp120 on relative CD4 binding ability (FIG. 4A) and a human monoclonal antibody to gp120 recognition (FIG. 4B).
Figure 4B:
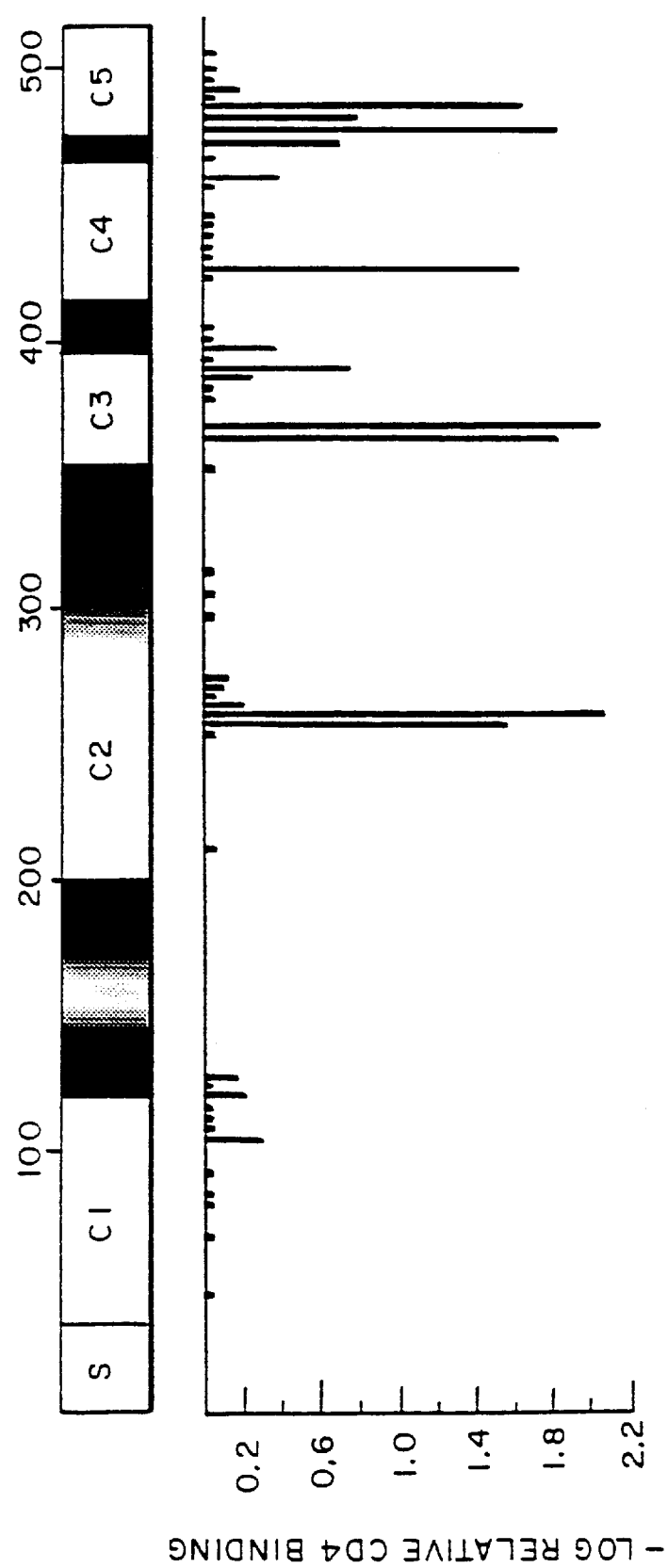

Single amino acid changes in thirteen residues resulted in glycoproteins that exhibited less than 50% of the CD4-binding ability of the wild-type gp120. The effects of the introduced changes on the processing of the gp160 precursor, the association of the gp120 molecule with the gp41 glycoprotein on the expressing cell, and the ability of two monoclonal antibodies that recognize conformation-dependent gp120 epitopes to precipitate the mutant glycoprotein were examined as described above with reference to FIG. 2. Several of the mutants (256 S/Y, 262 N/T, 384 Y/E, 447 S/I, 477 D/V and 482/483/484 ELY/GRA) exhibited greater than 60 percent reduction in either precursor processing or cell association that suggested the possibility that significant local or global conformational changes in gp120 resulted from these amino acid alterations. Recognition of the wild-type and all 13 mutant gp120 molecules by both monoclonal antibodies was similar, suggesting that gp160 precursor processing and cell association were more sensitive indicators of changes in envelope structure.

The most significant decreases in CD4-binding ability were observed for changes involving thr 257, asp 368, glu 370, and asp 457. Greater than 90% reduction in relative CD4-binding ability resulted from some of the mutations affecting these residues. The effects of the changes on gp160 processing and cell association of gp120 were small compared with those observed for other mutants exhibiting substantially greater CD4-binding ability (Table 2 and data not shown). Conversion of threonine 257 to arginine reduced CD4-binding ability by 84%, whereas more conservative changes to alanine or glycine resulted in a gp120 protein with nearly wild-type binding ability. These results indicate that while amino acid changes in this residue can dramatically disrupt CD4 binding, the presence of threonine is not indispensable for CD4 binding.

Some changes in the acidic residues in two regions of the gp120 glycoprotein, asp 368/glu 370 and asp 457, result in marked reduction in CD4 binding. Complete loss of detectable CD4 binding was associated with conversion of residues 368 or 370 to positively charged amino acids. Decreases in binding affinity were noted for other changes in these residues, even for the conservative change of glu 370 to aspartic acid.

Two classes of neutralizing antibodies are elicited against HIV-1 infected humans: type-restricted and broadly reactive. Type-restricted neutralizing antibodies arise early in infected humans and can be readily generated in animals by immunization with a variety of preparations of gp120 polypeptides [Putney, et al., *Science* 234:1392 (1986); Matthews, et al., *Proc. Natl. Acad. Sci. U.S.A.* 83:9709 (1986); Nara, et al., *Proc. Natl. Acad. Sci. U.S.A.,* 62:2622 (1988); Nara, et al., *J. Virol.* 61:3713 (1987); Goudsmit, et al., *Vaccine* 6:229 (1988)]. The best characterized of the type-restricted antibodies are those directed against the V3 variable region of gp120, Putney, et al. *Science* 234, supra; Matthews, et al., *Proc. Natl. Acad. Sci. U.S.A.,* 83, supra, Nara, et al., *Proc. Natl. Acad. Sci. U.S.A.* 62, supra; Nara, et al., J. Virol 61, supra; Goudsmit, et al., *Vaccine* 6, supra; Rusche, et al., *Proc. Natl. Acad. Sci, U.S.A.* 85:3198 (1988); Javaherian, et al., *Proc. Natl. Acad. Sci.,* 86:6768 (1989); Palker, et al., *Proc. Natl. Acad. Sci., U.S.A.,* 85:1932 (1988); Ho, et al., *J. Virol.* 61:2024 (1987); Knealy, et al., *AIDS Res. Hum. Retro.* 5:173 (1989)), which is contained within a loop formed by disulfide bonding [Leonard et al., *J. Biol. Chem.* 265:10373 (1990)]. Envelope glycoprotein variation within the linear epitope and outside the epitope can allow escape of viruses from neutralization by these antibodies [Looney, et al., *Science* 241:357 (1988); McKeating, et al., *AIDS* 3:777 (1989); Nara, et al., *J. Virol.* 64:3770 (1990)]. These antibodies do not block CD4 binding but apparently interfere with post-receptor binding events involved in virus entry and syncytium formation, presumably a component of the membrane fusion [Skinner, et al. *J. Virol.* 62:4195 (1988); Linsley, et al., *J. Virol.* 62:3695 (1988)].

Later in the course of HIV-1 infection of humans, antibodies capable of neutralizing a wider range of HIV-1 isolates appear [Nara, et al., *J. Virol* 61, supra; Goudsmit, et al., *Vaccine* 6, supra; Weiss, et al., *Nature* 316:69 (1985); Robert-Guroff, et al. *Nature* 316:72 (1985); Robert-Guroff, et al., *AIDS Res. Hum. Retro.* 4:343 (1988); Weiss, et al., *Nature* 324:572 (1986)]. These broadly-neutralizing antibodies have been difficult to elicit in animals, and are not merely the result of additive anti-V3 loop reactivities against diverse HIV-1 isolates that accumulate during active infection [Profy, et al., *J. Immunol.* 144:4641 (1990)]. A subset of the broadly reactive antibodies, found in most HIV-1 infected individuals, interferes with the binding of gp120 and CD4 [McDougal, et al., *J. Immunol.* 137:2937 (1986); Schnittman, et al., *J. Immunol.* 141:4181 (1988)]. This activity is observed only at low dilutions of patient sera, suggesting that the titer and/or affinity of these antibodies are low. These antibodies are present in individuals whose serum reacts only with native gp120, not with reduced gp120, suggesting that at least some of these antibodies recognize discontinuous gp120 epitopes [Putney, et al., *Science* 234:1392 (1986); Matthews, et al., *Proc. Natl. Acad. Sci. U.S.A.* 83, supra; Nara, et al., *Proc. Natl. Acad. Sci. U.S.A.* 62, supra; Haigwood, et al., in *Vaccines* 90:313 (Cold Spring Harbor Laboratory Press, 1990); Ardman, et al., *J. AIDS* 3:206 (1990)]. The discontinuous nature of the epitopes and the mixture of different antibodies found in patient serum has made characterization of the epitopes recognized by broadly-neutralizing antibodies difficult. Recently, human monoclonal antibodies derived from HIV-1-infected individuals that recognize the gp120 glycoproteins from a diverse range of HIV-1 isolates that block gp120-CD4 binding and that neutralize virus infection have been identified. One such human monoclonal antibody has been designated F105 [Robinson, et al. *AIDS Res. Hum. Retro.* 6:567 (1990); Ho, et al., *J. Virol.* 65:489 (1991); Tilley, et al, in *Retroviruses of Human AIDS and Related Animal Diseases* (eds. M. Girard and L. Valette, Paris (1990)].

The F105 antibody recognizes divergent HIV-1 isolates. Consequently, amino acids conserved among HIV-1 strains should constitute the critical components of the discontinuous F105 epitope. The gp120 amino acids important for recognition by the F105 antibody were identified by the reactivity of the antibody with a set of the HIV-1 gp120 mutants altered in conserved residues, discussed above.

Radiolabelled cell lysates from COS-1 cells transfected with plasmids expressing the wild-type or mutant envelope glycoproteins of the HXBc2 strain of HIV-1 were precipitated either with F105 antibody or with a mixture of sera derived from HIV-1-infected humans. Since the mixed patient sera recognize mutliple gp120 epitopes most of which are not affected by the amino acid changes in the mutant glycoproteins, the latter precipitation allows an assessment of the amount of mutant envelope glycoproteins present in the cell lysate. The F105 recognition index, which represents the ability of a given mutant envelope glycoprotein to be recognized by the F105 antibody relative to that of the wild-type envelope glycoprotein, was calculated as described in the legend to Table 3.

The results of the immunoprecipitation studies are shown in Table 3 and FIGS. 4A and 4B. FIGS. 4A and 4B show the effect of the amino acid changes in HIV-1 gp120 for relative CD4 binding ability and F105 recognition. The linear sequence of the HIV-1 gp120 molecule is shown in FIGS. 4A and 4B, with the conserved regions in light and the variable regions in dark shading. The positions of the signal sequence (S) and the conserved regions (C1-C5) are indicated, as are the amino acid numbers. Amino acid numbering is based on residue 1 corresponding to the initial methionine. Above the gp120 linear map is plotted the negative log of the relative CD4 binding ability observed for the most disruptive change at a given amino acid (FIG. 4A). The open bars indicate mutant glycoproteins that exhibited indices for gp160 precursor processing or gp120-gp41 association less than 40 per cent those of the wild-type values. Beneath the gp120 linear map is plotted the negative log of the recognition index for the F105 antibody observed for the most disruptive change at a given amino acid (FIG. 4B).

The F105 antibody precipitated both the gp160 and gp120 forms of the majority of the mutants at least as well as it did the wild-type envelope glycoproteins. Mutant glycoproteins with changes in amino acids 256–257, 368–370, 421, or 470–484 exhibited significant reductions in ability to be precipitated by the F105 antibody. In cases where multiple amino acid substituions at a single gp120 rsidue were examined, all of the changes in the above four regions resulted in significant decreases in F105 recognition. The conformation of most of the gp120 mutants exhibiting decreased F105 recognition was not grossly altered, as judged by the rate of envelope precursor processing, gp120-gp41 association, CD4 binding, or functional studies.

TABLE 3

F105 Recognition Indices and Relative CD4 Binding Abilities Of Selected HIV-1 gp120 Mutants[a]

| Mutant | F105 Recognition Index[b] | (Relative CD4 Binding Ability[c]) |
|---|---|---|
| Wild-type | 1.00 | (1.00) |
| 102 E/L | 0.45 | |
| 113 D/R | 0.92 | |
| 117 K/W | 0.60 | |
| 119–205[e] | >1.5 | (1.4) |
| 120/121 VK/LE | 1.21[d] | |
| 125 L/G | 0.67 | |
| 252 R/W | >1.5 | |
| 256 S/Y | <0.025 | (0.30) |
| 257 T/R | 0.0072 | (0.16) |
| 257 T/A | <0.078 | (1.12) |
| 257 T/G | <0.025 | (1.04) |
| 262 N/T | 0.60 | |
| 266 A/E | >1.5 | |
| 267 E/L | 0.80 | |
| 269 E/L | 0.76 | |
| 356 N/I | >1.5 | |
| 368 D/E | <0.024 | (0.09) |
| 368 D/T | <0.015 | (0.33) |
| 368 D/P | <0.015 | (0.09) |
| 368 D/R | <0.013 | (<0.004) |
| 368 D/N | 0.079 | (0.019) |
| 368 D/K | <0.02 | (<0.005) |
| 370 E/D | <0.017 | (0.45) |
| 370 E/Q | <0.038 | (0.018) |
| 370 E/R | <0.0075 | (<0.003) |
| 380/381 GE/YW | 1.5 | |
| 382 F/L | 0.54 | |
| 384 Y/E | 0.159 | |
| 386 N/Q | 1.00 | |
| 395 W/S | 0.44 | |
| 420 I/R | >1.5 | |
| 421 K/L | <0.020 | (0.55) |
| 427 W/S | >1.5 | (<0.006) |
| 427 W/V | >1.5 | (<0.012) |
| 456 R/K | >1.5 | |
| 457 D/A | 0.93 | (0.09) |
| 457 D/R | 0.42 | (0.15) |
| 457 D/E | 1.5 | |
| 457 D/G | 0.89 | |
| 463 N/D | 1.1 | |
| 465 S/L | >1.5 | |
| 470 P/G | 0.19 | (0.82) |
| 475 M/S | <0.013 | (1.03) |
| 477 D/V | 0.15 | (0.39) |
| 482/482/484 ELY/GRA | 0.018 | (0.44) |
| 485 K/V | >1.5 | |
| 491 I/F | 0.64 | |

[a]Other gp120 mutants tested for F105 recognition included 40 Y/D, 69 W/L, 76 P/Y, 80 N/R, 88 N/P, 103 Q/F, 106 E/A, 113 D/A, 207 K/W, 298 R/G, 308/309/310 RIQ/RPELIPVQ, 314 G/W, 314 G/Q, 380 G/F, 381 E/P, 386 N/R, 392 N/E + 397 N/E, 406 N/G, 429 K/L, 430 V/S, 432 K/A, 433 A/L, 435Y/H, 435 Y/S, 438 P/R, 450 T/N, 493 P/K, 495 G/K, 497/498/499 APT/VLL and 500/501 KA/KGIPKA. Precipitation of each of these mutants by the F105 antibody was at least as efficient as that seen for the wild-type glycoproteins.
[b]The F105 recognition index for a given mutant glycoprotein was calculated according to the following formula:

$$\text{F105 Recognition Index} = \frac{\text{mutant (gp160 + gp120)}}{\text{wild-type (gp160 + gp120)}} \times \frac{\text{wild-type (gp160 + gp120)}}{\text{F105 mutant (gp160 + gp120) Patien Serum}}$$

Immunoprecipitates of wild-type glycoproteins were analyzed on SDS-polyacrylamide gels and the relative intensity of envelope glycoprotein bands assessed by densitometric scanning of autoradiographs. Each value of for the recognition index represents the mean of at least two independent experiments, with experimental variation typically not more than 15% of the value reported.
[c]Relative CD4 binding abilities of mutant glycoproteins were taken from reference 21.
[d]The immunoprecipitation of the gp120 form of this mutant glycoprotein by the F105 antibody was decreased relative to that of the wild-type gp120 glycoprotein, although precipitation of the gp160 form of the mutant was slightly more efficient than that of the wild-type glycoprotein.
[e]The 119–205 mutant contains a deletion of the entire V1–V2 regions of HIV-1 gp120. The predicted amino acid sequence and the residue number near the deletion is . . . Leu (116)-Lys(117)-Pro(118)-Gly-Pro(206)-Lys(207) -Val(208)-Ser(209) . . .

Table 3 indicates that some of the gp120 mutants poorly recognized by the F105 antibody retain CD4-binding ability and, in other studies, some of these mutants exhibited significant envelope glycoprotein function. This suggested that several of the mutants might escape neutralization by the F105 antibody. We employed an assay in which an env-defective HIV-1 provirus encoding the bacterial chloramphenicol acetyltransferase (CAT) gene was complemented for a single round of replication by the wild-type or mutant envelope glycoproteins [Helseth, et al., J. Virol. 64:2416 (1990)]. The recombinant viruses containing the mutant envelope glycoproteins and packaging the env-defective provirus encoding the bacterial CAT gene were produced in COS-1 cells. The virions were incubated at 37° C. for one hour in the presence or absence of a high concentration (80 micrograms/ml) of purified F105 antibody prior to incubation with Jurkat lymphocytes. Two days after infection, Jurkat cells were lysed and CAT activity measured. See FIG. 5. The percentage of the CAT activity observed for each mutant in the presence of the antibody relative to the CAT activity observed in the absence of antibody is shown.

Viruses containing the wild-type envelope glycoproteins were neutralized by the F105 antibody, as were viruses containing mutant envelope glycoproteins that were recognized as well as the wild-type glycoproteins by the F105 antibody (FIG. 5). By contrast, viruses containing the 257 T/G, 257 T/R, 368 D/N, 368 D/T, 370 E/Q, 421 K/L and 475 M/S mutant envelope glycoproteins, were significantly more resistant to neutralization by the F105 antibody compared with virions containing the wild-type glycoproteins. Some of the latter mutants (257 T/G, 475 M/S) remained sensitive to neutralization by the 0.5 βmonoclonal antibody, which recognizes the V3 loop of HIV-1 gp120 [Matsushita, et al, *J. Virol* 62:2107 (1988)], indicating that the escape from neutralization was antibody-specific (data not shown). The 470 P/G and 477 D/V mutant glycoproteins, which exhibited an F105 recognition index between that of the wild-type and 475 M/S glycoproteins, exhibited an intermediate level of sensitivity to F105 neutralization.

The results reported herein identify several non-contiguous gp120 amino acids (epitopes) important for CD4 binding. It is unlikely that the observed decreases in CD4 binding affinity are simply a result of gross conformational changes in the mutant gp120 proteins. We have studied gp120 molecules derived from gp160 precursor proteins that have undergone proteolytic cleavage and transport to the cell surface, processes that are known to strongly select for correctly folded glycoproteins. Such constraints on transport appear to be far less restrictive when truncated soluble forms of gp120 are made. Further, the gp120 mutants markedly reduced for CD4 binding still associate with the expressing cell, an interaction dependent on the gp41 exterior domain and on discontinuous regions located at both the amino and carboxy termini of gp120. Third, reactivity of the gp120 mutants that exhibit diminished CD4 binding with the two monoclonal antibodies that recognize conformationally dependent gp120 epitopes was maintained, although this parameter was insensitive to gp120 structural changes relative to precursor processing or cell association.

Figure 2:
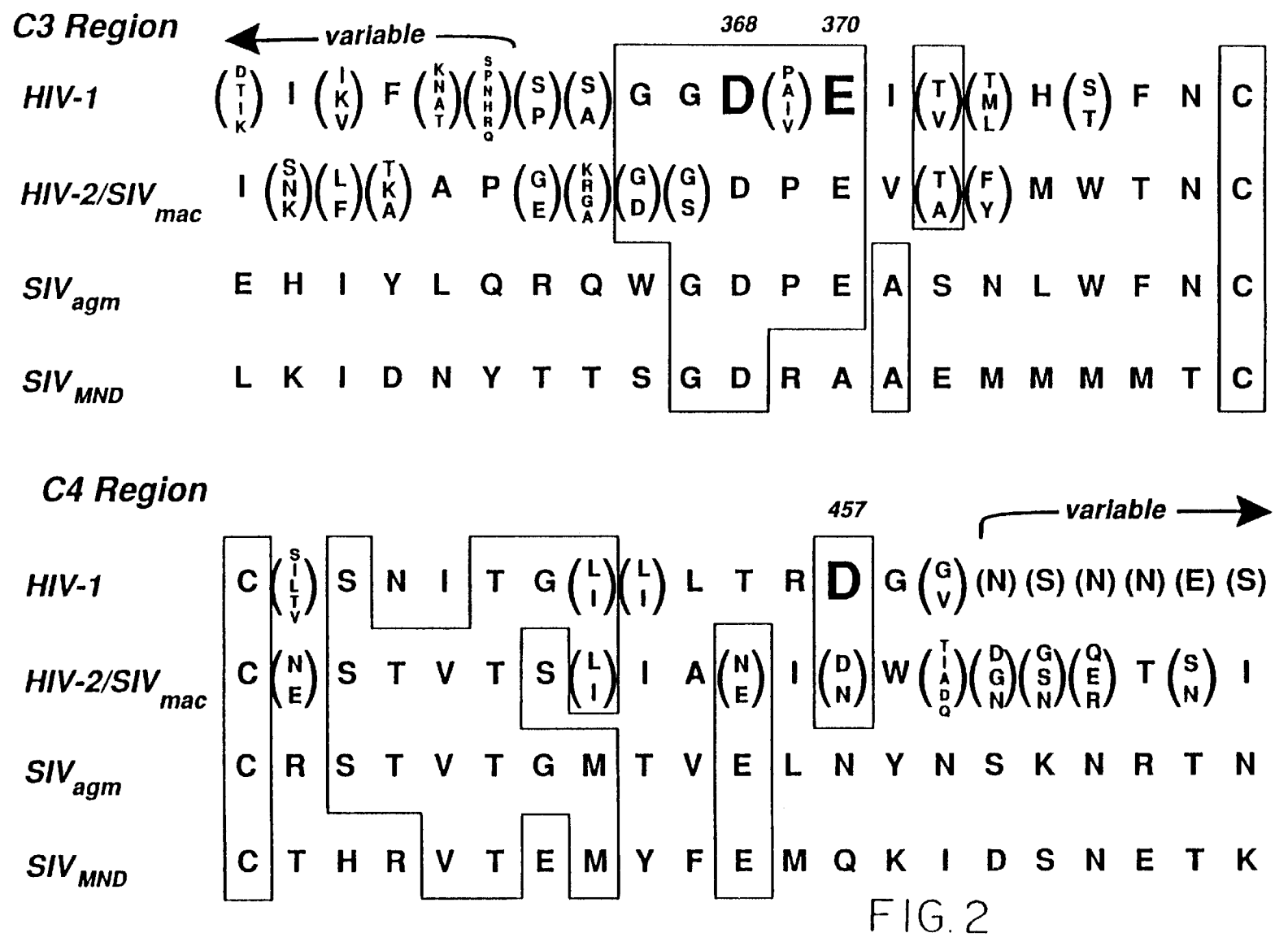

Of the gp120 amino acids conserved among primate immunodeficiency viruses, changes in asp 368, glu 370 and asp 457 exert the greatest effect on CD4 binding. These acidic residues are located within the proteolytic fragment reported to retain CD4-binding ability. Sequence comparison of primate immunodeficiency viruses indicates that the presence of a carbonyl group, rather than the acidic group, in the side chain of residue 457 is a conserved feature. FIG. 2 provides a sequence comparison of primate immunodeficiency viruses near the 368/370 and 457 residues (shown in boldface type). Identical amino acids are boxed, while different residues found at each position for different isolates are included in parentheses. Regions of hypervariability are indicated. For the C4 region of hypervariability in HIV-1, only the HXB2 sequence is shown in parenthesis due to the extreme degree of variability in this region.

While residues exhibit moderate variability, amino acids 368 and 370 are invariant in all viruses, except for SIV$_{MND}$, where a glutamic acid is positioned two residues carboxy-terminal to the 370 position. The alteration of either the 368 or 370 acidic side chain to a basic side chain is especially disruptive of CD4-binding ability. This result suggests that the presence of a charged residue in these positions is not sufficient for CD4 binding, and that the acidic side chains may participate in ionic bonds, either with CD4 or with other gp120 regions. The CD4 region important for gp120 binding [Peterson, A., et al., *Cell* 54:65–72 (1988); Landau, N., et al., *Nature* 334:159–162 (1988); Jameson, B., et al., *Science* 240:1335–1338 (1988); Clayton, L., et al., *Nature* 335:363–366 (1988); Arthos, J., et al., *Cell* 57:469–481 (1989); Mizukami, T., et al., *Proc. Natl. Acad. Sci., U.S.A.* 85:9273–9277 (1988)] contains several basic residues that might require neutralization by acidic amino acids to stabilize the gp120-CD4 interaction.

The 368–370 and 457 residues, although distant on the linear gp120 sequence, may be proximal on the native molecule. Although not wishing to be bound by theory, this model is supported by the observation that the gp120 cystine residues at 378 and 445 are disulfide-linked, which suggests that these two regions may form a symmetrical structure. FIG. 3 shows a predicted symmetrical structure formed by the C3 and C4 gp120 regions. The known disulfide bond between cys 378 and cys 445 occurs within a hydrophobic region encompassed by the solid line. Residues 368, 370 and 457 are contained within hydrophilic regions depicted outside the solid line. Sequences predicted to form β-turns [Modrow, S., et al.,*J. Virol.* 61, supra are illustrated as bends in the figure. Hypervariable regions (V3 and V5) [Myers, G., et al., supra] are boxed, and sites of known glycosylation are depicted as ball-and sticks.

The characteristics described are predictive of exposure on the surface of the native molecule. The hydrophilic properties and β-turn potential of these two regions suggests that they may be efficient B cell epitopes, and thus constitute important targets for immunoprophylaxis or immunotherapy. The immunogenicity of the 368–370 and 457 gp120 regions during natural HIV-1 infection may be modified by the proximity of these residues to highly variable regions that contain potential N-linked glycosylation sites (FIG. 3).

One mutation affecting gp120 residue 257, which is not contained within the gp120 proteolytic fragment reported to bind CD4, significantly affects CD4 binding.

Antibodies directed against the gp120 region encompassing residues 423–438 interfere with CD4 binding. However, changes in the most highly conserved amino acids within this region of gp120 exert only small effects on CD4 binding, although single amino acid changes in the less well-conserved trp 427 and ala 433 residues have been reported to affect CD4 binding.

Amino acid changes in HIV-1 gp120 residues located in four discontinuous regions resulted in dramatic reductions in recognition by a broadly neutralizing human monoclonal antibody, F105. That multiple substitutions in the same residues reduced F105 recognition in the apparent absence of global conformational disruption of gp120 and that functional neuralization escape mutants were generated by some changes in each of these regions indicates these four regions constitute critical elements of a discontinuous epitope. This model is consistent with that of other characterized discontinuous epitopes on proteins, which are typically comprised of 13–24 amino acids derived from two to five continuous components [Colman, et al, *Nature* 326:358 (1987); Bhat, et al., *Nature* 347:483 (1990); Sheriff, et al., *Proc. Natl. Acad. Sci. U.S.A.* 84:8075 (1987); Laver, et al., *Cell* 61:553 (1990); Bentley, et al, *Nature* 348:254 (1990); Amit, et al., *Science* 233:747 (1986); Padlan, et al., *Proc. Natl. Acad. Sci. U.S.A.* 86:5938 (1989); Patterson, et al., *Science* 249:755 (1990)].

Significant overlap exists between gp120 regions implicated in CD4 binding and those important for F105 recognition, which is consistent with the ability of the F105 antibody to block gp120-CD4 interation. Two elements of the F105 discontinuous epitope at 256–247 and 368–370 correspond precisely to the gp120 amino acids identified as important for binding CD4. Recognition by the F105 antibody was more sensitive to different substitutions at these residues than was CD4 binding. A third element of the F105 discontinous epitope at lysine 421 is adjacent to tryptophan 427, changes in which results in dramatic reductions in CD4-binding ability but not F105 recognition. Thus, the F105 antibody apparently recognizes a more hydrophilic segment in the fourth conserved gp120 region than does CD4. The inclusion of these three discontinuous regions important in CD4 binding within a discontinuous antibody epitope suggests that they are proximal on the native glycoprotein.

The fourth element of the discontinuous epitope at gp120 residues 470–484 does not overlap the region near aspartic acid 457, which is important for CD4 binding, but there are reasons to believe that these two regions are proximal on the native gp120 glycoprotein. Both hydrophilic regions, which symmetrically flank the short fifth variable region of gp120, exhibit strong β-turn potential, which could result in the apposition of these regions in the native glycoprotein. Supporting this notion is the observation that some of the more conformationally disruptive changes in aspartic acid 457 (e.g., 457 D/R) affect F105 recognition, while some of the more conformationally disruptive changes in the 470–484 regions (e.g., 477 D/V or 482/483/484 ELY/GRA) exhibit small effects on CD4 binding [Olshevsky, et al., J. Virol. 64:5701 (1990)].

This data suggest that interference with CD4 binding is a major mechanism of virus neutralization by at least one gp120 antibody, the F105 antibody. Since the components of the gp120 structure required for binding F105 and CD4 differ, neutralization escape by variation within the components of the F105 epitope was possible. The high degree of conservation of these regions observed in HIV-1 isolates suggest either that selective pressure for change in these regions is low, that constraints on such change exist that are not modeled in these in vitro replication assays, or that other mechanisms for neutralization escape exist. Since neutralization escape is theoretically possible even for an antibody recognizing a conserved functional gp120 structure, as has been seen for antibodies directed against variable gp120 regions [Looney, et al., Science 241, supra; McKeating, et al., AIDS 3, supra; Nara, et al., J. Virol. 64, supra] and for infected patient sera [Reitz, et al, Cell 54:57 (1988)], HIV-1 variation should be considered in therapeutic or prophylactic applications. It remains to be seen whether HIV-1 variation will prove to be a problem for in vivo use of monoclonal antibodies directed against these epitopes or for in vivo vaccine applications. However, an antibody that recognizes the reported CD4 binding epitope region has been shown, herein, to neutralize divergent HIV-1 strains.

It is evident that those skilled in the art, given the benefit of the foregoing disclosure may make numerous modifications thereof, and departures from the specific embodiments described herein, without departing from the inventive concepts, and the present invention is to be limited solely by the scope and spirit of the appended claims.

We claim:

1. An immunogenic gp120 polypeptide from HIV-1, HIV-2 or SIV comprising conserved regions which have at least one of variable regions V1, V2 or V3 deleted and replaced by a linker sequence, wherein the linker sequence comprises amino acids that maintain the overall 3-dimensional structure of gp120 by permitting turns in the tertiary structure.

2. The immunogenic polypeptide of claim 1 wherein said conserved regions are C1, C2, C3, C4 and C5.

3. The immunogenic polypeptide of claim 1 wherein the polypeptide has at least one gp120 amino acid residue which is a sugar addition site deleted.

4. The immunogenic polypeptide of claim 1 wherein amino acid residues corresponding to the HIV-1 gp 120 env protein amino acid residues 256–257, 368–370, 421, 427, 454, 470–484 are present and can define a discontinuous epitope.

5. The immunogenic polypeptide of claim 4, wherein a cysteine residue is present in either the first, second, penultimate or last position on the polypeptide.

6. The immunogenic polypeptide of claim 5, wherein the cysteine residue is present in the first or penultimate position on the polypeptide.

7. The immunogenic polypeptide of claim 1 wherein both the V1 and V2 regions have been removed and inserted therefore is a gly amino acid residue.

8. The immunogenic polypeptide of claim 4, wherein a mutation in at least one site selected from the group of HIV-1 gp120 amino acid residues consisting of residues 266, 356, 381, 427, 432, 435, 438, 493 and 495 is present.

* * * * *